United States Patent
Klöffel et al.

(10) Patent No.: US 11,305,043 B2
(45) Date of Patent: Apr. 19, 2022

(54) METHOD FOR REGULATING A HEATING DEVICE FOR HEATING A FLUID FOR A DIALYSIS FLUID CIRCUITY, CONTROL DEVICE AND BLOOD TREATMENT APPARATUS

(71) Applicant: Fresenius Medical Care Deutschland GmbH, Bad Homburg (DE)

(72) Inventors: Peter Klöffel, Nüdlingen (DE); Helmuth Ender, Zeil am Main (DE); Michael Schlereth, Schweinfurt (DE); Christoph Bardorz, Rottendorf (DE); Walter Ehrenberger, Gerolzhofen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 811 days.

(21) Appl. No.: 16/071,202

(22) PCT Filed: Jan. 27, 2017

(86) PCT No.: PCT/EP2017/051848
§ 371 (c)(1),
(2) Date: Jul. 19, 2018

(87) PCT Pub. No.: WO2017/129791
PCT Pub. Date: Aug. 3, 2017

(65) Prior Publication Data
US 2021/0170086 A1 Jun. 10, 2021

(30) Foreign Application Priority Data
Jan. 29, 2016 (DE) .......................... 102016101648.9

(51) Int. Cl.
*A61M 1/16* (2006.01)

(52) U.S. Cl.
CPC ........ *A61M 1/1662* (2014.02); *A61M 1/1635* (2014.02); *A61M 2205/3306* (2013.01); *A61M 2205/3389* (2013.01)

(58) Field of Classification Search
CPC .. A61M 1/1662; A61M 1/1635; A61M 1/166; A61M 1/1686; A61M 2205/3306; A61M 2205/3389
See application file for complete search history.

(56) References Cited

U.S. PATENT DOCUMENTS 3,730,183 A 5/1973 Goldsmith et al.
4,715,398 A 12/1987 Shouldice et al.
(Continued)

FOREIGN PATENT DOCUMENTS

CN 202146468 U 2/2012
CN 204910171 U 12/2015
(Continued)

OTHER PUBLICATIONS

International Preliminary Report on Patentability in International Application No. PCT/EP2017/051848, dated Jul. 31, 2018, 7 pages (English Translation).
(Continued)

*Primary Examiner* — John Kim
(74) *Attorney, Agent, or Firm* — Fish & Richardson P.C.

(57) ABSTRACT

The present disclosure relates to a method and system for regulating and/or monitoring a heating device for heating a fluid, which has flowed in an in-flow section of a dialysis fluid circuit. The dialysis fluid circuit is part of a blood treatment apparatus, which comprises a container for receiving the fluid and a heating container for heating the fluid. The method encompasses the step of starting a heating process for heating the fluid in the heating container. The fluid is in fluid communication with the container when the (Continued)

filling level of the container reaches a pre-determined filling level value by means of direct or indirect flow from the inlet.

12 Claims, 4 Drawing Sheets

(56) References Cited

U.S. PATENT DOCUMENTS

| | | |
|---|---|---|
| 4,718,022 A | 1/1988 | Cochran |
| 4,769,151 A | 9/1988 | Shouldice |
| 4,894,164 A | 1/1990 | Polaschegg |
| 2013/0259458 A1 | 10/2013 | Beisser et al. |

FOREIGN PATENT DOCUMENTS

| | | |
|---|---|---|
| DE | 3736713 | 5/1988 |
| JP | S56-158256 U | 11/1981 |
| JP | S60-14863 | 1/1985 |
| JP | S63-178307 | 7/1988 |
| JP | H08-033707 | 2/1996 |
| JP | 2011-200312 | 10/2011 |
| WO | WO 2014/052596 | 4/2014 |

OTHER PUBLICATIONS

International Search Report and Written Opinion in International Application No. PCT/EP2017/051848, dated Mar. 30, 2017, 8 pages (English Translation).

METHOD FOR REGULATING A HEATING DEVICE FOR HEATING A FLUID FOR A DIALYSIS FLUID CIRCUITY, CONTROL DEVICE AND BLOOD TREATMENT APPARATUS

CROSS-REFERENCE TO RELATED APPLICATIONS

The present application is the national stage entry of International Patent Application No. PCT/EP2017/051848, filed on Jan. 27, 2017, and claims priority to Application No. DE 10 2016 101 648.9, filed in the Federal Republic of Germany on Jan. 29, 2016, the disclosures of which are incorporated herein in entirety by reference.

TECHNICAL FIELD

The disclosure relates to methods and systems for regulating and/or monitoring a fluid heating device.

BACKGROUND

Dialysis fluids for blood treatment apparatuses may be provided in different ways prior to being introduced into a dialysis fluid circuit. For example, water may be withdrawn or removed from an external water supply system and prepared for the dialysis fluid circuit. Such preparation may be executed in a flow circuit or in a water inlet system in which various preparation steps for producing the dialysis fluid are executed. The water or the finished dialysis fluid is then heated by a heating device and introduced into the dialysis circuit, in which a blood filter or dialyzer is integrated.

SUMMARY

A method is proposed by the present disclosure for controlling or regulating (the expressions "controlling" or "regulating" are to be understood herein as being alternative or interchangeable, both modes are encompassed by the present disclosure) and/or for monitoring a heating device for heating a fluid which flows or has flowed through an inlet into an in-flow section of a dialysis fluid circuit. The fluid may be water, e.g. conveyed from an external water supply system. The dialysis fluid circuit is part of or is connected to a blood treatment apparatus. The dialysis fluid circuit comprises a container for receiving the fluid and a heating container for heating the fluid, wherein the heating container is in fluid communication with the container.

The method encompasses starting a heating process for heating the fluid in the heating container when the filling level of the container has reached a pre-determined filling level value (or pre-determined filling level), by a, particularly direct or indirect, inflow, at least once or for the first time.

Some or all of the steps of the method may be run in an automated manner, e.g. prompted by a correspondingly programmed or configured control device or regulating device (the expressions "control device" and "regulating device" are to be understood herein as being alternative or interchangeable). The control device may be programmed and/or configured to initiate or introduce, effect, execute or perform the steps of the method.

The blood treatment apparatus comprises at least a control device or is connected thereto in signal communication.

A digital, particularly a non-volatile, storage medium, particularly a machine-readable data storage device, particularly in form of a floppy disk, CD, EPROM or DVD, with electronically or optically readable control signals may interact with a programmable computer system such that the machine-induced steps of a method are prompted.

A computer program product comprises a program code that is volatile or saved on a machine-readable medium or a signal wave for prompting the machine-induced steps of the method when the computer program product runs on a computer. A computer program product can be understood, for example, as a computer program which is stored on a storage device, as an embedded system as a comprehensive system with a computer program (e.g. an electronic device with a computer program), as a network of computer-implemented computer programs (e.g. a client-server system, a cloud computing system, etc.), or as a computer on which a computer product is loaded, executed, saved or developed.

The term "machine-readable medium" as used herein denotes in certain exemplary embodiments a medium containing data or information being interpretable by software and/or hardware. The medium may be a data medium or carrier, like a (floppy) disk, a CD, DVD, a USB stick, a flashcard, an SD-card or the like.

A computer program comprises a program code for prompting the machine-induced steps of the method when the computer program runs on a computer. A computer program can be understood as, for example, a physical, ready-for-distribution software product which comprises a computer program.

It also applies to the digital storage medium, the computer program product and the computer program that all or some of the machine-executed steps of the method are prompted. In particular, this is the case in the interaction with a blood treatment apparatus, as described.

In all of the statements, the use of the expression "may be" or "may have" and so on, is to be understood synonymously with "preferably is" or "preferably has," and so on respectively, and/or is intended to illustrate a further exemplary embodiment.

Embodiments may encompass some or all of the following features in arbitrary combination provided such a combination be not recognized by the person skilled in the art to be technically impossible.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" always as "at least one". This understanding is also equally encompassed by certain aspects as the interpretation that a numeric word, for example, "one" may alternatively mean "exactly one", wherever this is evidently technically possible for the person skilled in the art. Both are encompassed by some embodiments and apply herein to all used numerical words.

The indication of "top" and "bottom", are to be understood herein, in case of doubt by the person skilled in the art, as absolute or relative spatial indications, which refer to the orientation of the respective component during its use as intended.

In some exemplary embodiments, the in-flow section to the dialysis fluid circuit is a water circuit or a water inlet system. The in-flow section may be described as a hydraulic system. The inlet may be an inlet from an external water supply system or from a water line system. The inlet may be a water inlet.

In the following, the term "fluid" shall be used synonymously with the term "water", however, without thereby limiting the fluid to water. The fluid may also be another medium and in particular another liquid, provided it be suitable for an in-flow section to the dialysis fluid circuit.

In some exemplary embodiments, the pre-determined filling level value is reached when the filling level changes from a filling level which corresponds to a filling level value below the pre-determined filling level value—at which the container is comparatively empty—to a filling level at which the container is comparatively full and which corresponds to a filling level value being at or above the predetermined filling level value.

In some exemplary embodiments, the pre-determined filling level value is a limit or threshold.

In some exemplary embodiments, the filling level value indicates, when it is reached "coming from below", that the container is completely filled. Alternatively, regardless of the actual filling level of the container, it is assumed that the container is sufficiently or completely filled when the pre-determined filling level value is reached.

In some exemplary embodiments, the filling level value indicates, when it is reached "coming from above", that the container is empty. Alternatively, regardless of the actual filling level of the container, it is assumed that the container is not sufficiently or insufficiently filled when the filling level goes or falls below the pre-determined filling level value.

"Empty" and "filled" are not to be limited to the understanding that e.g. in an empty container there is no fluid at all resp. that no further fluid could be added into the container in a filled state.

Reaching the filling level value or falling below it may rather be understood as information for the control device which reacts to such information, e.g. by opening or closing a valve to an inlet.

In some exemplary embodiments, the filling level value indicates that the container is completely filled. Alternatively, regardless of the actual filling level of the container, it is assumed that the container is sufficiently or completely filled when the pre-determined filling level value is reached.

In some exemplary embodiments, the heating process is started only when the filling level has reached the pre-determined filling level value several times, in particular two, three, four or five times.

In some exemplary embodiments, starting the heating process for heating the fluid in the heating container starts only after an inflow into the in flow section and/or after an outflow from the container has been prevented or did not happen, e.g. after stopping the dialysis apparatus or the inflow, e.g. because of an alarm.

In some exemplary embodiments, starting the heating process for heating the fluid in the heating container begins only if in addition (or once in addition) a fluid flows from a balancing chamber of the blood treatment apparatus. This applies in particular after the flow from the balancing chamber has been prevented or did not happen.

With a balancing chamber a pre-determined volume is pumped, wherein there are valve switch phases between phases in which the volumes are pumped, in which valve switch phases the valves of the balancing chamber are switched. No flow can take place during the valve switch phases. However, these valve switch phases belong, in the sense of this description, to those phases in which there is a flow. In a continuously operating balancing chamber, there is, in other words according to this description, a flow also present during the valve switch phases and starting the heating will not be controlled in or during these valve switch phases according to the method, if this causes a short-termed stop of the flow. In this sense, phases, in which—due to the design or to the controlling of the pump device or the balancing chamber—a discontinuous or pulsatile flow is generated, are to be understood also as flow phases, i.e. not as phases in which the flow from the balancing chamber was interrupted or stopped.

In some exemplary embodiments, the heating container is arranged upstream or downstream of the container, both containers are in fluid communication by means of one or several connecting lines. The container and the heating container may be a one-unit design and may be directly connected to each other. The container and the heating container may be arranged in one unit or in one housing and may be in fluid communication with each other e.g. by means of a dividing wall and/or an overflow system and/or a tubing system or a pipe system.

In some exemplary embodiments, starting the heating process strengthens the heating efforts, starting from a low heat level at which the heating device, even without a sufficient filling level or fluid in the heating container, is not damaged because of an excess or too-high heating and e.g. because of damage of the heating container, in which the fluid flows during normal operation and is heated by means of the heating device, or because of a blown heating rod. In these embodiments, starting the heating activities may be understood as leaving a stand-by heating mode.

In some exemplary embodiments, the heating device may be a heating rod. This heating rod may be inserted from the bottom or from the top into the heating container. The heating rod may be designed such that it comprises two areas. The heat-generating element, e.g. a heating spiral, is arranged in the first area, and this element is contacted with the outside in the second area. In this, the first area is arranged at the far end of the heating rod away from the contact. In case the heating rod is inserted from the bottom, a reduction of the liquid level below the level of the heating rod respectively the formation of an air cushion or air pocket at the upper end of the heating rod will directly cause that a highly heated area of the first area of the heating rod is not covered with liquid, therefore, leading to quickly or more quickly to a potential damage due to overheating. When the heating rod is inserted from the top, first the second area is cleared of fluid so that an air pocket in the heating container may less rapidly lead to the problem of damage due to overheating.

In some exemplary embodiments, stopping the heating process decreases or reduces the heating efforts, starting from a high heating level and/or e.g. transferring the heating activity into a heating mode, in which the heating device is not damaged, even without a sufficient filling level or fluid in the heating container, due to excess heating and e.g. because of a blown heating rod or because of overheating. In these embodiments, stopping the heating activity may be understood as a transfer e.g. to a stand-by heating mode.

In some exemplary embodiments, the heating process is started only when the filling level first drops below the pre-determined filling level value and subsequently, i.e. after a filling of the container, reaches or exceeds the predetermined filling level value. In other words, the filling level in these embodiments must first drop to a filling level which e.g. indicates an empty or a non-sufficiently or insufficiently filled container. Subsequently, i.e. only after the container was initially not sufficiently filled, the container is filled to reach at least the pre-determined filling level or filling level value; and only after having reached the latter, the heating process starts. Such procedure ensures that the heating container must definitely be filled and starting the heating process with an empty heating container can be excluded. This is particularly true when the heating container is arranged upstream of the container. It can be expected in this case that the container can only be filled when the heating container is filled as well. This ensures that the heating process is only started when the heating container is sufficiently filled.

In some exemplary embodiments, the filling level of the container is determined by a mechanical filling level meter, a conductivity sensor, an optical sensor or any arbitrary combination thereof. A mechanical filling level meter is e.g. a float which moves with a filling level. By means of a position sensor attached to or connected to the float, the filling level may be forwarded as electrical signal to a regulating device or a control device. The mechanical filling level meter can be described as a mechanical sensor.

The filling level meter may comprise a switch, e.g. a float switch. When the switch is open, the container is then considered filled and/or the pre-determined level value is considered to be reached. When the switch is closed, then the container is refilled. With that, it is ensured that the filling volume does not fall below a certain level value having the advantage that this offers the required reaction time and, hence, the heating container does not run dry. A circuit, connected to the switch, may be configured to take into account a certain hysteresis such that there is no unnecessary refilling when the water filling level moves or changes.

In some exemplary embodiments, the fluid from the inlet is first stored in a fluid reservoir. Subsequently, the fluid flows into the heating container and afterwards flows from the heating container into the container by means of an overflow.

In some exemplary embodiments, the fluid is additionally heated by a heat exchanger. The heat exchanger may forward dialysate (i.e. spent dialysis fluid or dialysis fluid withdrawn from the dialyzer) from the dialysis fluid circuit and transfer the heat of the dialysate to the fluid. The dialysate may then be disposed of downstream of the heat exchanger.

In some exemplary embodiments, the fluid which has been heated by the heating device and/or by the heat exchanger is conveyed by a balancing chamber from the in-flow section of the dialysis fluid circuit into the dialysis fluid circuit.

In some exemplary embodiments, the heating container comprises a temperature sensor configured for measuring the temperature of the fluid in the heating container.

In some exemplary embodiments, to start the heating process the filling level of the container must have reached or exceeded the predetermined filling level value over a period of time T1, in particular in a recirculation mode.

Starting the heating after a pre-determined time period may be activated in particular in a recirculation mode. The blood treatment apparatus may be operated in different modes, e.g. a treatment mode and a recirculation mode. In the treatment mode, fluid is added to and withdrawn from the hydraulic system, comprising the in-flow section and the dialysate circuit, while the fluid is circulated in the recirculation mode without having fluid being added to or withdrawn from the system. Thereby, the level in the container remains mostly constant, wherefore the filling level meter or float indicates a "filled" container. This recirculation mode may be activated e.g. at least during a cleaning mode, in particular a hot cleaning, in which cleaning mode the heating device must be started even when the filling level meter or float does not make any movement which would indicate a filling process of the container. In order to allow a start of the heating at a constant filling level, the above-mentioned starting is allowed in this mode after the end of a pre-determined period of time during which the pre-determined filling level value was continuously reached.

In some exemplary embodiments, at least one of the following steps is controlled or regulated by the control device: Starting or terminating the heating process in the heating container; monitoring the filling level in the container or the filling level meter; and opening or closing a check valve for filling the fluid reservoir and/or the container through the inlet.

In some exemplary embodiments, the blood treatment apparatus comprises at least the container, a unit for detecting if the pre-determined filling level value of the container is reached, a heating container, being in fluid communication with the container, having a heating device for heating the fluid and a device for transferring or conveying the fluid into the dialysis fluid circuit of the blood treatment apparatus.

In some exemplary embodiments, the unit for filling or transferring the fluid into the dialysis fluid circuit comprises, or is designed as, a balancing chamber.

In some exemplary embodiments, the blood treatment apparatus comprises a reservoir which is arranged to be filled with fluid, e.g. from an inlet or from an external inlet.

In some exemplary embodiments, the blood treatment apparatus comprises a heat exchanger and/or at least a connection for adding a concentrate.

In some exemplary embodiments, the fluid is stored in a fluid reservoir in a first step, before it actively or passively overflows in a second step from the fluid reservoir into the container for determining the fluid filling level. In these embodiments there is no heating container arranged between the fluid reservoir and the container. The heating container may be arranged downstream of the container.

In some exemplary embodiments, the heating container is arranged downstream of the container.

In some exemplary embodiments, the in-flow-section of the dialysis fluid circuit comprises a degassing chamber for degassing the fluid and/or at least one air separation chamber.

For example, a negative pressure in the fluid is created by means of a degassing throttle arranged in a fluid-conducting line, and thus gas (mostly air) is released from the fluid. The released gas is collected in the degassing chamber arranged downstream thereto. In an air separation chamber arranged further downstream the gas may be led away by an outlet line. Air from other sources, e.g. from feeding concentrate lines, may still be trapped, collected and separated in the air-separation chamber. Degassing and/or air separation may advantageously prevent introducing air into the dialysis circuit.

The blood treatment apparatus may be used for dialysis, hemodialysis, hemodiafiltration, filtration, or apheresis.

In some exemplary embodiments, the control device is programmed for controlling and/or regulating single parameters. The parameter states may relate to e.g. switching on/off the heating device. The control device may comprise an electric circuit with a power supply for the supply of voltage. The control device may be referred to a controller or control equipment. Triacs (Triodes for alternating current) may be used for controlling the heating device. Hence, switching on or switching off the heating process in the heating container may be controlled and/or regulated by the control device.

Furthermore, the filling level meter may be monitored and/or a check valve for filling the fluid reservoir may be opened or closed by the control device.

In several exemplary embodiments, the measuring unit, the mechanical fluid level meter and/or the mechanical sensor has/have only two different, mutually exclusive, binary states, e.g. pre-determined filling level H1 reached or not, container full or not, container empty or not. Thereby, in several embodiments, the measuring unit, the mechanical fluid level meter and/or the mechanical sensor transfer to the control device a control signal which only distinguishes between two states. This control signal encompasses in several embodiments, for example, that the measuring unit, the mechanical fluid level meter and/or the mechanical sensor display a hysteresis, i.e. that the state depends on a previous state. For example, the state "container full" may have another threshold value when the latter is reached from above as when it is reached from below. In several exemplary embodiments the hysteresis is generated wholly or at least partly by the control device.

In several embodiments, the measuring unit is no device which may take more than two states. In particular, the measuring unit is no Hall effect position detector in such embodiments.

In several exemplary embodiments, the control device has no proportional-integral-derivative-controller (PID-controller), in particular not for the water inflow.

In several exemplary embodiments, a controller of the control device, in particular for the water inflow, is no steady controller, in particular no unsteady controller, in particular no two-point-controller.

In several exemplary embodiments, the container and/or the heating container is no degassing chamber and/or air separation chamber.

In several exemplary embodiments, there is a degassing chamber and/or air separation chamber upstream and/or downstream the container and/or the heating container.

In several exemplary embodiments, the measuring unit, the mechanical fluid level meter, the mechanical sensor and/or the float are arranged in the container and, in particular, not in a degassing chamber and/or in an air separation chamber upstream or downstream the container.

In several exemplary embodiments, the container and/or the heating container contain no bodies, particularly no plastic bodies, for degassing the liquid present in the container. In particular, the container and/or heating container contains in several exemplary embodiments no bodies made from polypropylene, e.g. cylinders and/or spheres.

In several exemplary embodiments, the control device does not switch on and/or off a valve in the inlet in, or during, a period of fixed length.

In several exemplary embodiments, the control device does not calculate any switch relation and/or any duty factor of the valve in the inlet. In several exemplary embodiments, there is no sensor in the inlet measuring the inflow of the fluid from the inlet into the container or into the fluid reservoir. In other embodiments at least one such sensor exists.

In several exemplary embodiments, the control device controls the state of the heating without dependency on a flow measured in the inlet.

Some or all of the embodiments may comprise one or several of the above-mentioned or the following advantages.

The method may advantageously prevent damage of the heating device and/or of the heating container, which are provided in an in-flow section of a dialysis fluid circuit for heating a fluid.

The method may advantageously prevent an overheating of the heating device due to e.g. a too-early heating or to a heating taking place at an undesired time. This may be, for example, the case after fluid has been conveyed from the in-flow section into the dialysis fluid circuit and there is not yet a sufficient volume of fresh fluid, e.g. having flowed from the inlet into the heating container. Such state, which may be referred to as running dry, may in any case however lead to a non-sufficiently filled heating container. Operating the heating device while the heating container is not at least sufficiently filled may damage the heating device. This should be avoided for safety reasons, economical reasons and/or medical reasons. Some embodiments may contribute to preventing such damage. Further, starting the heating device while there is no flow may lead to local heating of the fluid which may lead to damaging the heating container or the tubes connected thereto. In extreme cases, heating may lead to an evaporation of the fluid. A heating of an empty heating container may also cause damage, wherein it is advantageously possible to make sure, by means of the method, that the heating container is filled. In some embodiments, the conveyed volume may additionally be selectable such that the heating container must advantageously be filled.

BRIEF DESCRIPTION OF THE DRAWINGS

The present disclosure shall be hereinafter exemplarily explained based on the accompanying illustrations in which identical reference numerals refer to same or similar elements. The following applies in the partially strongly simplified figures.

DETAILED DESCRIPTION

Figure 1:
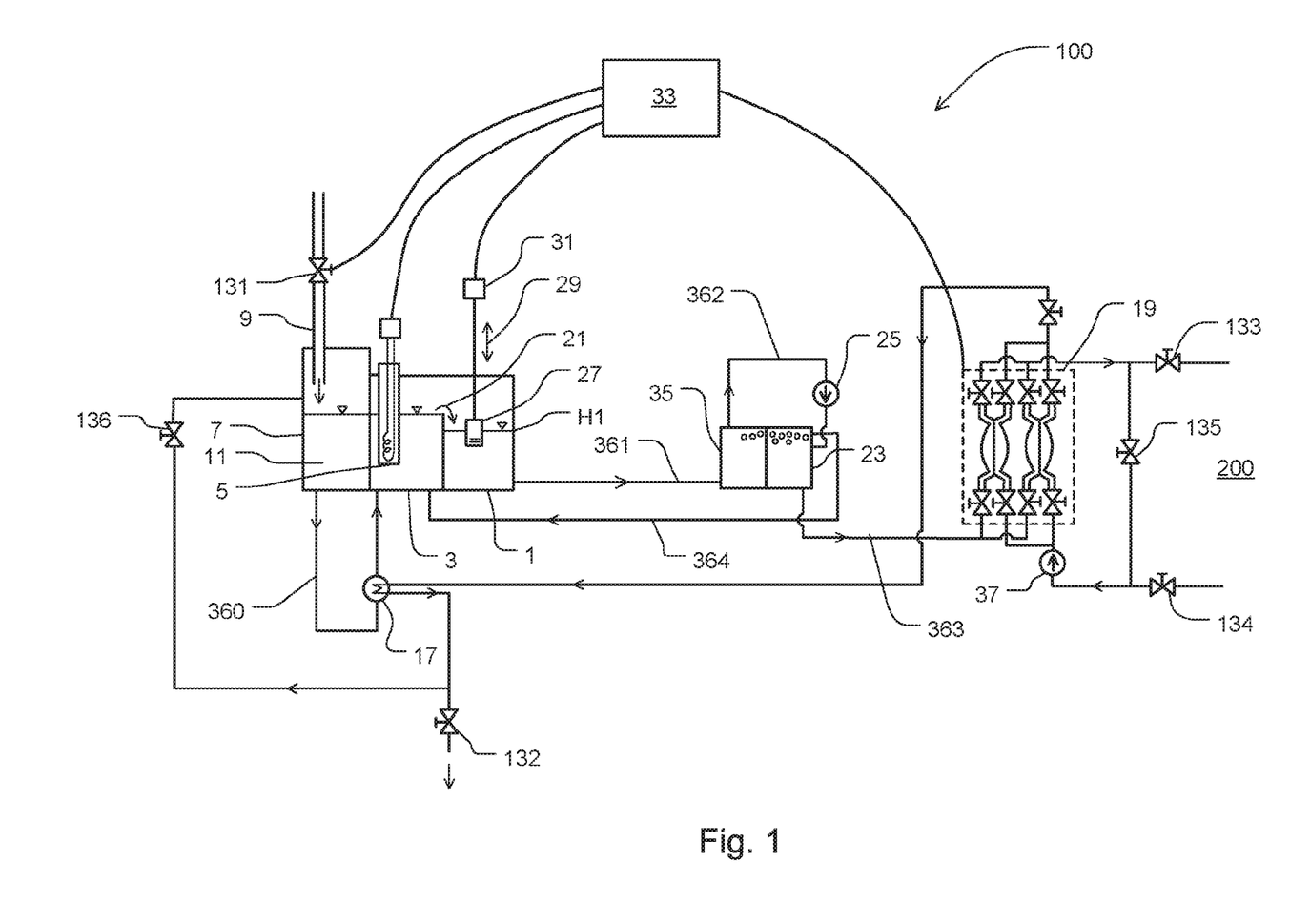
FIG. 1 shows an apparatus of a first embodiment of the blood treatment apparatus having a container for measuring the filling level and, upstream thereto, a heating container comprising a heating device.

FIG. 1 shows an apparatus 100 in a first purely exemplary embodiment, having a container 1 for a fluid 11. The apparatus 100 is connected to, or is part of, a blood treatment apparatus 200. The container 1 is used at least for measuring the filling level of the fluid 11. The filling level is based on or refers to the container 1, hence, measuring is done in the container 1. The apparatus 100 further comprises a heating container 3 arranged upstream (in FIG. 1 left) of the container 1 and having a heating device 5 for warming or heating the fluid 11, if contained in the heating container 3. The container 1 and the heating container 3 are in this embodiment embodied as one unit (as one physical unit), by way of example.

A reservoir 7 may further be arranged upstream of the heating container 3 into which the fluid 11 may flow from an inlet 9. The inlet 9 may be referred to as an external inlet 9, as here the fluid 11 may exemplarily be supplied through an external line section, e.g. a water supply system. The inlet 9 may be opened or closed by a check valve 131.

In the embodiment of FIG. 1, the inlet 9 is connected to the water supply system. The fluid 11 is thus water and shall be hereinafter referred to as water 11. The fluid should however not thereby be limited to water. The water 11 may optionally flow through a connecting line 360. The connecting line 360 may be arranged between the heating container 3 and the reservoir 7, from the reservoir 7 into the heating container 3. Likewise, there may be a direct connection between the heating container 3 and the reservoir 7, e.g. by a partially permeable dividing wall between the two containers. The connecting line 360 is optionally connected to a heat exchanger 17. The flow direction of the water 11 is indicated by arrows. The water level in the heating container 3 and in the reservoir 7 is optionally the same, i.e., there is a pressure equalization between both containers by means of the connecting line 360. The heat exchanger 17 may, in addition to the heating device 5, heat the water 11. The warmer fluid perfusing the heat exchanger 17 is conveyed to the heat exchanger 17 from a balancing chamber 19 and it is in particular a spent dialysate from a dialysis fluid circuit of the blood treatment apparatus 200, not shown in FIG. 1, and arranged downstream of the balancing chamber 19. The dialysate flows after having perfused the heat exchanger 17 e.g. into a disposal system. Purely exemplary, a further check valve is comprised in the outlet line of the heat exchanger 17. "Spent dialysate" hereby refers to the dialysate which perfuses at least one or more sections of the dialysis fluid circuit, which during a treatment are arranged downstream of the dialyzer used for the blood treatment. The dialyzer is therein arranged downstream of the valve 133 and upstream of the valve 134.

The water 11 further heated in the heating container 3 by the heating device 5 flows via an overflow, indicated by an overflow direction 21, into the container 1. The water level or filling level of the container 1 is determined by a sensor or filling level meter, which is in FIG. 1 purely exemplarily embodied as a mechanical filling level meter 27, which may be referred to as a mechanical sensor or float 27. The filling level meter 27 may alternatively or additionally be e.g. a conductivity sensor, an optical sensor or another sensor.

The position of the float 27 changes in a vertical shift direction 29 of the float 27 according to the filling level or level in the container 1. A schematically illustrated measuring unit 31 detects, in particular a pre-determined, filling level H1 which indicates or signals a filled or at least a largely filled container 1. The float 27 may, in another embodiment which is not shown herein, alternatively measure or signal the respective current position of the float 27 by means of the schematically illustrated measuring unit 31. The measuring signal of the measuring unit 31 is forwarded to a control or regulating device 33 (short: control device 33). Different measuring signals may be received, processed and outputted by or in the control device 33.

The heated water 11 flows from the container 1 through a connecting line 361 into a degassing chamber 35. A degassing throttle, which may release gas from water by means of negative pressure, may optionally be arranged in the connecting line 361. The gas released from the water 11 is collected into the degassing chamber 35, said gas rises upward in the degassing chamber 35 (this is indicated by small bubbles in the upper area of the degassing chamber 35).

Subsequently, the water 11 flows through a further connection line 362 into an air separator 23. A pump 2 is arranged in the connecting line 362. By means of this pump 2, the water 11 is pumped or conveyed at least from the container 1 into the degassing chamber 35, from there into the air separator 23 and from there, through a further connecting line 363, further into the balancing chamber 19. At least a portion of the water 11 may optionally be conveyed from the air separator 23, through the connecting line 364, back into the heating container 3. For example, water 11, highly mixed with foam, which should not reach the balancing chamber 19 through the connecting line 363, may be returned.

At least the control signal for switching on or switching off the heating device 5 is to be included in the control or regulating signals (in short: control signals) which are outputted by the control device 33. Furthermore, the check valve 131, for opening and closing the inlet 9, as well as the balancing chamber 19 may be controlled or actuated, e.g. for opening and closing single or several valves.

The heating process for warming or heating the water 11 in the heating container 3 is only started by switching on the heating device 5, when the filling level in the container 1 has reached a pre-determined filling level H1.

In an exemplary embodiment of the method, the heating device 5 is started as described below—for example by switching on or connecting the heating triodes for alternating current in the power supply by means of a processor in the control device 33. The float 27 may in a starting position, first adopt any position which is above or below the pre-determined filling level value H1, e.g. in the lower area of the container (this would signal an empty container 1), a middle position or another position. Should the float 27 reach at least the pre-determined filling level H1, this indicates an achieved inflow into the container 1. This inflow is achieved through the inlet 9 while valve 131 is open. The inflow into the container 1 is not achieved directly from the inlet 9, rather indirectly through the reservoir 7, the heating container 3 and the overflow 21. The pre-determined filling level value H1 may represent an upper limit of the float 27. When the pre-determined filling level value H1 is reached, the heating process for heating the water 11 in the heating container 3 starts.

Optionally, there should be no other active signals prior to switching on the heating device 5, e.g. a flow alarm or a water alarm, indicating a shortage or lack of water 11 at another site or location, e.g. in the reservoir 7 or in the connecting line. In an exemplary embodiment, in the recirculation mode, the in-flow section is completely filled with water 11 (or another fluid), the check valve 131 is closed permanently and the connection to the blood treatment apparatus 200 is short-circuited. This short-circuiting of the connection to the blood treatment apparatus 200 is achieved by closing the valves 133 and 134 and opening the valve 13, by way of example.

Alternatively, the short circuit is past the two valves 133 and 134, i.e. for example downstream of valve 133 and upstream of valve 134 (unlike what is shown herein). Optionally, there is no need for a valve 13. In this embodiment the short-circuit may be made in that the ends of the dialysis circuit which are connected during treatment to the dialyzer are or will be directly or indirectly interconnected to each other.

Furthermore, the outlet line of the heat exchanger 17 is closed by valve 132. The water 11 flowing from the heat exchanger 17 is returned back into the reservoir 7 by opening the valve 136. A closed circuit is achieved in the in-flow section by means of this arrangement. Thus, the float 27 signals permanently the pre-determined filling level value H1. Reaching or exceeding the filling level value H1 by an inflow is thus not possible in the recirculation mode. Despite the absence of the feature "reaching the filling level H1", the heating device 5 should permanently be switched on in order e.g. to be able to clean the in-flow section with a heated water 11. To ensure this permanent heating in the recirculation mode by the control device 33, the control device 33 may comprise various switch modes. A switch mode may, over a scheduled period of time, e.g. provide that a variable is queried which recognizes a detection of reaching or exceeding the predetermined filling level value H1 of the float 27. The scheduled period of time may purely exemplarily be 10 seconds, 12.5 seconds or 15 seconds. Since no filling level value H1 is reached in the recirculation mode, this state may indicate or signal the recirculation mode and thus switch on the heating process or keep the latter permanently switched on. During the recirculation mode, the heating container 3 is likewise permanently filled or is permanently perfused. The flow or the perfusion is achieved in the recirculation mode by a pump 2.

The balancing chamber 19 is filled through the connecting line 363 by a pressure, applied by the pump 2, and with respective opened valves. When the chambers are filled with water 1 (which may be referred to as fresh dialysate) from the in-flow section, the valves which were open for filling will be closed. When the spent dialysate is to be subsequently or at a later point of time drained from the dialysate circuit of the connected blood treatment apparatus 200, the pump 37 forwards this to be-drained dialysate into the area of the balancing chamber 19 which is separated from water 11. Through such forwarding of dialysate into the balancing chamber 19, the fresh dialysate is concurrently drained from the balancing chamber 19 into the dialysate circuit. This is achieved in that the chambers with the fresh and the spent dialysate are separated by a membrane and through the active application of pressure on one chamber side, the other chamber side, in appropriate valve positions, is emptied.

Figure 2:
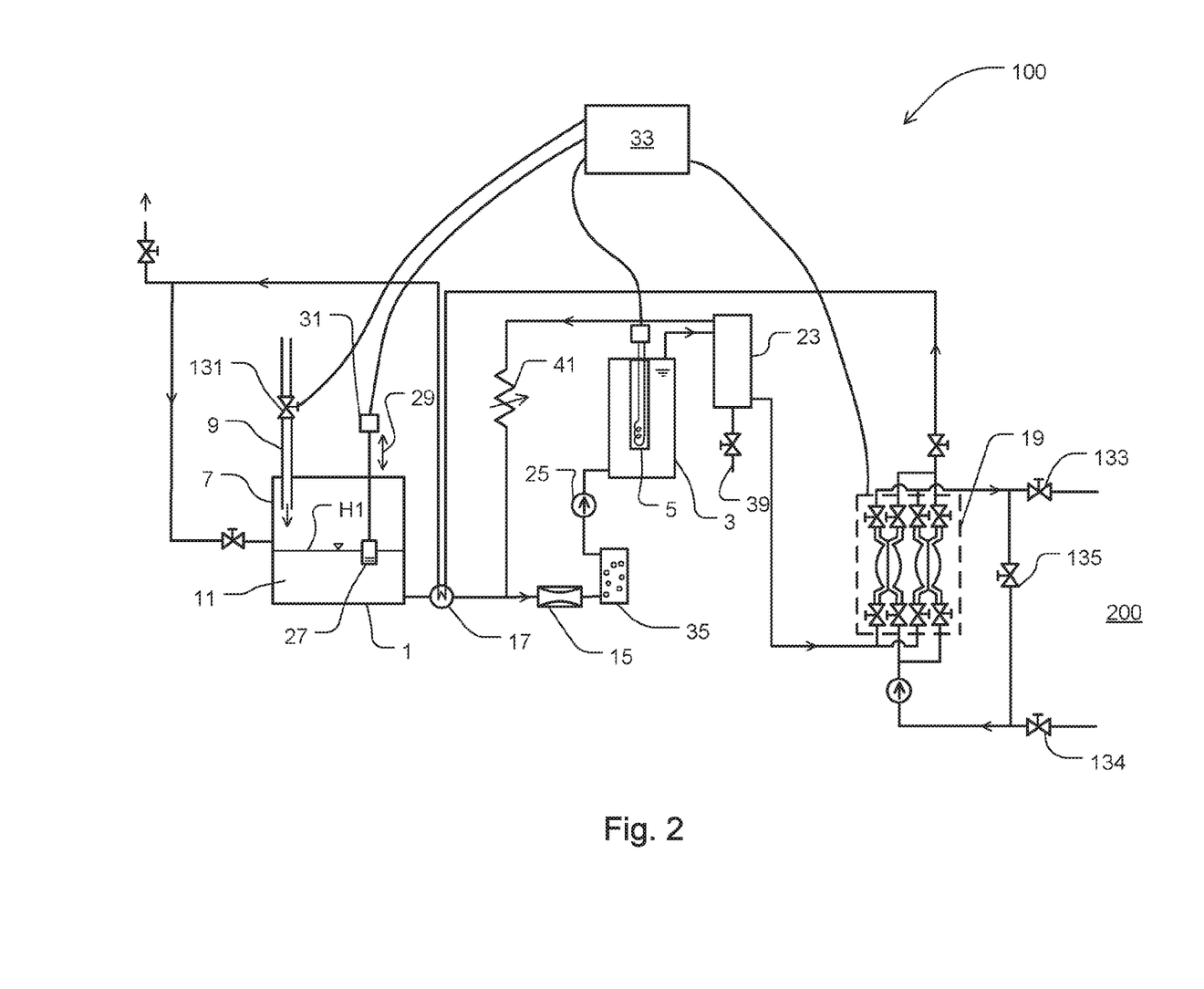
FIG. 2 shows an apparatus of a second embodiment of the blood treatment apparatus having a container for measuring the filling level and, downstream thereto, a heating container comprising a heating device.

FIG. 2 shows a device 100 of a second embodiment having a container 1 for measuring the filling level and a heating container 3 arranged downstream thereto comprising a heating unit. The device 100 is connected to a blood treatment apparatus 200. The container 1 and the heating container 3 are unlike in FIG. 1 not embodied as one physical unit, rather as spatially separated from each other.

Water 11 is led into the container 1 through the inlet 9 and a controllable valve 131. The filling level (or level) may be determined there by the float 27 and the measuring unit 31. The float 27 rises or sinks in the vertical shift direction 29 depending on the filling level. Water 11 flows from the container 1 through a connecting line with an interconnected heat exchanger 17, in which the water 11 may be warmed up in addition to the heating device 5, and with a degassing throttle 15 into the degassing chamber 35. First a pump 2 and subsequently the heating container 3 filled with water 11 and with the heating device 5 are arranged downstream to the degassing chamber 35. An air separator 23 is arranged further downstream. Fluids, for example concentration solutions, may be added to the water 11 in the air separator 23 through a connection 39 in order for said water to be used as dialysis fluid. A connecting line in the lower area of the air separator 23 leads to the balancing chamber 19. Water 11 may by means of this line be added as a fresh dialysis fluid to a dialysis fluid circuit through the balancing chamber 19. A connecting line in the upper area of the air separator 23 leads initially to an optional pressure limiting valve 41 and leads subsequently into the connecting line between the container 1 and the degassing chamber 35.

The measurement signal of the measuring unit 31, which indicates the pre-determined filling level value H1 of the float 27 in container 1, may be detected by the control device 33. The control device 33 may output a control signal for switching on/off the heating device 5, control the opening and closing of the check valve 131 and regulate the balancing chamber 19 for supplying fluid 11 from the air separator 23.

In an exemplary embodiment, the heating device 5 is started by switching on a heating relay in the control device 33. The heating relay shall, however, in this exemplary embodiment be activated only when the pre-determined filling level value H1 in the container 1 has been reached several times after the float has intermediately dropped below the pre-determined filling value H1. For example, it may be provided that the heating relay is started by the control device 33 only when the filling level initially falls below the pre-determined filling level value H1, then e.g. rises above four times and falls intermediately below this value. Alternatively, the heating relay may begin after the sequence has run with an initiative rising above, subsequently falling below and then rising above four times, with an intermediate falling below and reaching the predetermined filling level value H1 repeatedly.

In this present exemplary embodiment, there is a direct relationship and/or connection between the float 27 resp. the measuring unit 31 for detecting the current float position on the one hand side and the controlling of the check valve 131 for opening and closing of the inlet 9 on the other hand side. The check valve 131 of the inlet 9 is controlled by the current position of the float 27 or by the reaching of the pre-determined filling level value H1. In an error-free operation, the check valve 131 opens when the float 27 is low. If water 11 flows in, then the float 27 rises. If, however, the check valve 131 of the inlet 9 remains open longer than a pre-determined period of time, e.g. longer than 10 seconds, 11 seconds, or 12 seconds, and the float 27 does still not rise, then this may indicate a problem with the water supply through the inlet 9. For example, the water supply may in principle be interrupted in such case as this may be the case in a burst pipe, a line blockage or another problem. Recognizing an interrupted water supply is particularly important as an empty heating container 3 and a switched-on heating device 5 may result in damages to the heating device 5.

By means of the control device 33, it is first checked, for example by an electronic circuit, if the float 27 is at the pre-determined filling level value H1, which indicates a filled container 1. If the test result is negative, i.e. the pre-determined filling level value H1 is not reached, the balancing chamber 19 is thus not activated and no water 11 may be conveyed as dialysis fluid into the dialysis circuit arranged downstream of the balancing chamber 19. If this situation continues for long, e.g. longer than 10 seconds, 11 seconds or 12 seconds, then a water-shortage alarm may be triggered. If the test result is however positive, i.e. the pre-determined filling level value H1 is reached, then the balancing chamber 19 is activated and this water volume is optionally withdrawn from e.g. the air separator 23 after each filling cycle of the balancing chamber 19. After that, the filling level of the float 27 falls below the pre-determined filling level value H1 and water is refilled through the inlet 9 by opening the check valve 131. If the filling level does not reach again the pre-determined filling level value H1 within the specified time period, e.g. 11 s, a water-shortage alarm is activated. The water-shortage alarm is automatically deactivated when the water flows in again and the pre-determined filling level value H1 is reached anew.

A water-excess alarm may also be displayed besides the described water-shortage alarm. A water-excess alarm is triggered whenever the pre-determined filling level value H1 is displayed permanently over a longer period of time. Various reasons may be responsible and shall be described hereinafter. Normally, the filling level of the float 27 drops after each filling cycle of the balancing chamber 19 through which filling cycle a certain pump volume is conveyed from the in-flow section into the dialysis fluid circuit. However, if the filing level of the float 27 does not drop even after a second filling cycle of the balancing chamber 19, there may be a fault in the device and a water-excess alarm is optionally triggered or displayed. The check valve 131 of the inlet 9 is in this case optionally closed by the control device 33. The water-excess alarm is automatically deactivated when the filling level of the float 27 drops again. The water-excess alarm may furthermore be confirmed by a user through pushing a "dialysis start switch", whereby two further pump cycles of the balancing chamber 19 are permitted through which further water is withdrawn resp. added to the dialysis fluid circuit. The heating device 5 is in this stage already deactivated or switched off by the control device 33.

Monitoring the filling level of the float 27 may be carried out as described, e.g. based on a period of time of about 12 seconds to trigger an alarm (water-shortage alarm or water excess alarm). However, this does not apply to the recirculation mode or cleaning mode, for example, for the hot rinsing. The heating device 5 must be constantly switched on in this mode. The control device 33 monitors the recirculation mode and switches the float 27 or the measuring unit 31 permanently to "filled", "up" or to the pre-determined filling level value H1, without an inflow through inlet 9 taking place. A separate switch, which may be e.g. likewise arranged in the control device 33, activates or deactivates the recirculation mode.

Reference is made to the description of FIG. 1 for further explanations of the recirculation mode.

Figure 3:
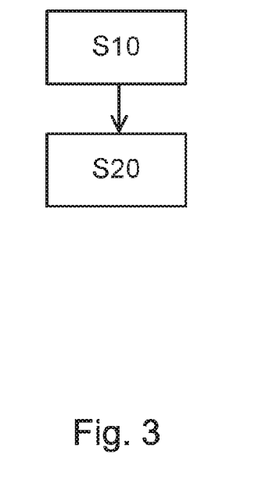
FIG. 3 shows, schematically simplified, an exemplary embodiment of the method which encompasses detecting a filling level change and starting a heating process.

FIG. 3 shows schematically simplified an exemplary embodiment of the method comprising a detecting of a change of the filling level in the container 1 (S) and starting a heating process (S20). A change of the filling level is in particular reaching (and displaying) the pre-determined filling level value H1. Reaching the pre-determined filling level value H1 is to be understood as reaching "at least once". A repeated reaching requires an intermediate drop of the filling level under the predetermined filling level value H1. Therefore, starting the heating process in certain embodiments may be initiated only after a repeated reaching of the pre-determined filling level value H1.

Figure 4:
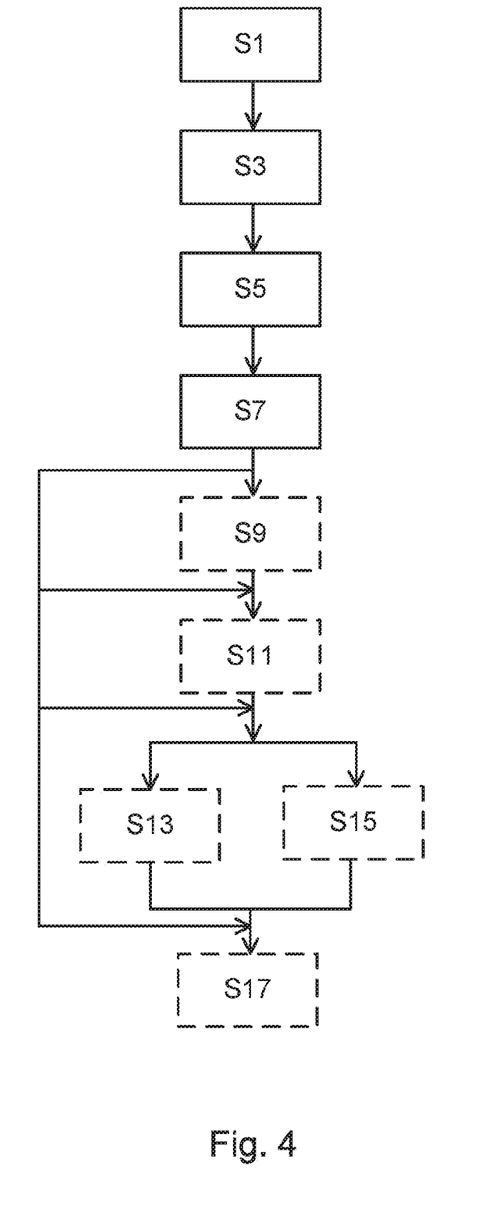
FIG. 4 shows, schematically simplified, an exemplary embodiment of the method for regulating and/or monitoring a heating device for heating a fluid.

FIG. 4 shows a schematic illustration of an exemplary embodiment of the method using a device 100 which is connected to, or is part of, a blood treatment apparatus 200.

The method encompasses in an optional step S1 detecting a pre-determined filling level value H1 in the container 1 of the device 100. The fluid 11 may be water, however without being limited thereto. The fluid 11 may be a mixture of liquids.

In step S3, the method encompasses starting the filling of the container 1 when the filling level is below the pre-determined filling level value H1. The filling of the container 1 may encompass for example opening a check valve 131 of the inlet 9. The process of filling and of opening the valve 131 requires that the filling of the balancing chamber 19 is first stopped or terminated. During a previous filling of the balancing chamber 19, the inlet 9 resp. the valve 131 must in turn be closed.

In step S5, the method encompasses heating the fluid 11 in the heating container 3, or the beginning thereof, when the filling level of the container 1 reaches the predetermined filling level value H1.

In step S7, the method encompasses an optional monitoring of the filling level of the container 1. If the filling level drops below the pre-determined filling level value H1, e.g. because of withdrawal of water for filling the dialysis fluid circuit, then the heating process is stopped or interrupted. The heating process may also be completely stopped, i.e. finally terminated.

In a further embodiment, the method may optionally encompass the step S9, in which the heating process starts only when the filling level first drops below the pre-determined filling level value H1 and subsequently, after a filling of the container 1, reaches the pre-determined filling level value H1. The method may encompass in an embodiment the optional step S11, in which the water in the water inlet system may be degassed by the degassing chamber 35 for degassing the water 11 and/or by the air separation chamber 23 for separating the air comprised in the water.

The method may in an embodiment encompass the optional step S13, wherein the water 11 from the inlet 9 is stored, in a previous step, in a fluid reservoir 7, wherein water 11 flows or is conveyed from the fluid reservoir 7 by an overflow into the container 1 for determining the filling level of the water 11.

In a further embodiment, the method may encompass the optional step Sas an alternative to step 13. In step S15, the water 11 from inlet 9 is first stored in the fluid reservoir 7, subsequently, the water 11 flows into the heating container 3 and afterwards flows from the heating container 3 into the container 1 by means of an overflow.

The method may in an embodiment encompass the optional step S17, in which water 11 is additionally heated by a heat exchanger 17, wherein the heat exchanger 17 is perfused by dialysate from the balancing chamber 19.

LIST OF REFERENCE NUMERALS

100 Apparatus
200 Blood treatment apparatus
H1 Pre-determined filling level
S1-S20 Method steps
1 Container
3 Heating container
5 Heating device
7 Reservoir; fluid reservoir
9 Inlet; external inlet
11 Fluid; water
131, 132, 133, 134, 13, 136 Valve; check valve
15 Degassing throttle
17 Heat exchanger
19 Balancing chamber
21 Overflow direction
23 Air separator; air separation chamber
25 Pump in the in-flow section
27 Mechanical filling level meter; mechanical sensor; float
29 Vertical shift direction of the float
31 Measuring unit
33 Control device
35 Degassing chamber 360, 361, 362, 363, 364 Line; connecting line
37 Pump in the dialysate circuit
39 Connection
41 Pressure control valve

The invention claimed is:

1. A method for regulating and/or for monitoring a heating device for heating a fluid that has flowed and/or is flowing, via an inlet, into an in-flow section of a dialysis fluid circuit, wherein the dialysis fluid circuit is part of a blood treatment apparatus, wherein the dialysis fluid circuit comprises a container for receiving the fluid, and a heating container for heating the fluid, the method comprising:
determining a filling level of the fluid in the container; and
in response to determining that the filling level of the fluid in the container has reached a pre-determined filling level value, starting a heating process for heating the fluid in the heating container, which is in fluid communication with the container by the inlet, wherein the heating process is started only when the filling level of the fluid in the container is determined to have reached the pre-determined filling level value.

2. The method according to claim 1, wherein the heating process starts only when the filling level has reached the pre-determined filling level value at least two times.

3. The method according to claim 2, wherein the heating process for heating the fluid in the heating container starts after an inflow into the in-flow section and/or an outflow out of the container has been prevented.

4. The method according to claim 1, wherein the heating process for heating the fluid in the heating container starts after an inflow into the in-flow section and/or an outflow out of the container has been prevented.

5. The method according to claim 1, wherein the heating process for heating the fluid in the heating container starts only when or after a fluid flows out of a balancing chamber.

6. The method according to claim 1, wherein the reaching of the pre-determined filling level value in the container is determined by at least one of a mechanical filling level meter, a conductivity sensor, or an optical sensor.

7. The method according to claim 1, wherein the fluid from the inlet is stored in a fluid reservoir wherein the fluid flows from the reservoir into the heating container and flows out of the heating container into the container by overflowing out of the heating container.

8. The method according to claim 1, wherein the fluid is additionally heated by a heat exchanger, wherein the heat exchanger is perfused by dialysate.

9. The method according to claim 1, further comprising:
monitoring the filling level in the container, wherein the heating process is paused or stopped when the filling level falls below the pre-determined filling level value.

10. The method according to claim 1, wherein starting the heating process for heating the fluid in the heating container comprises:
reaching the pre-determined filling level value of the container over a period of time T1 before starting the heating process.

11. The method according to claim 10, wherein the pre-determined filling level value of the container is reached over the period of time in a recirculation mode.

12. The method according to claim 1, wherein at least one of the following steps is controlled or regulated by a control device:
starting or terminating the heating process in the heating container;
monitoring the filling level in the container; and
opening and closing a check valve for filling a fluid reservoir and/or filling the container from the inlet.

* * * * *